US008918170B2

(12) United States Patent
Brunswick et al.

(10) Patent No.: US 8,918,170 B2
(45) Date of Patent: Dec. 23, 2014

(54) ELECTROPHYSIOLOGICAL ANALYSIS SYSTEM

(71) Applicant: Impeto Medical, Paris (FR)

(72) Inventors: Philippe Brunswick, Paris (FR); Nicolas Bocquet, Chatillon (FR)

(73) Assignee: Impeto Medical, Paris (FR)

( * ) Notice: Subject to any disclaimer, the term of this patent is extended or adjusted under 35 U.S.C. 154(b) by 0 days.

(21) Appl. No.: 14/173,317

(22) Filed: Feb. 5, 2014

(65) Prior Publication Data

US 2014/0194714 A1    Jul. 10, 2014

Related U.S. Application Data

(63) Continuation of application No. 12/527,415, filed as application No. PCT/EP2008/052211 on Feb. 22, 2008, now Pat. No. 8,655,443.

(30) Foreign Application Priority Data

Feb. 23, 2007    (FR) .................................... 07 53461

(51) Int. Cl.
*A61B 5/05*    (2006.01)
*A61B 5/145*    (2006.01)
*A61B 5/053*    (2006.01)

(52) U.S. Cl.
CPC ............... *A61B 5/14539* (2013.01); *A61B 5/05* (2013.01); *A61B 5/053* (2013.01)
USPC ......................................................... 600/547

(58) Field of Classification Search
USPC ........................................................ 600/547
See application file for complete search history.

(56) References Cited

U.S. PATENT DOCUMENTS 3,821,949 A    7/1974    Hartzell et al.
4,365,637 A    12/1982    Johnson
(Continued)

FOREIGN PATENT DOCUMENTS

WO        WO-00/19894 A1        4/2000
WO        WO 2006136598      *   6/2006
(Continued)

OTHER PUBLICATIONS

Millasseau, Sandrine C. et al.; "Contour analysis of the photoplethysmographic pulse measured at the finger," Journal of Hypertension, vol. 24, No. 8, Aug. 2006, pp. 1449-1456.

(Continued)

*Primary Examiner* — Max Hindenburg
*Assistant Examiner* — Renee Danega
(74) *Attorney, Agent, or Firm* — Harness, Dickey & Pierce, P.L.C.

(57) ABSTRACT

The invention provides an electrophysiological analysis system, in particular for detecting pathological states. This system comprises: electrodes intended to be placed in different regions of the body that are well away from each other; an adjustable DC voltage source for generating successive DC voltage pulses varying in magnitude from one pulse to another, the duration of the pulses being equal to or greater than about 0.2 seconds; a switching circuit for selectively connecting a pair of active electrodes to the voltage source and for connecting at least one other high-impedance electrode; and a measurement circuit for recording data representative of the current in the active electrodes and potentials on at least certain high-impedance connected electrodes in response to the application of said pulses. The range of voltages covered causes, from one pulse to another, the appearance or disappearance of electrochemical phenomena in the vicinity of the active electrodes.

19 Claims, 7 Drawing Sheets

(56) References Cited

U.S. PATENT DOCUMENTS

| | | | |
|---|---|---|---|
| 4,509,531 | A | 4/1985 | Ward |
| 4,690,152 | A | 9/1987 | Juncosa |
| 4,794,934 | A | 1/1989 | Motoyama et al. |
| 5,307,817 | A | 5/1994 | Guggenbuhl et al. |
| 5,406,956 | A | 4/1995 | Farwell |
| 5,771,261 | A | 6/1998 | Anbar |
| 5,782,884 | A | 7/1998 | Stotts et al. |
| 5,800,350 | A | 9/1998 | Coppleson et al. |
| 5,928,155 | A | 7/1999 | Eggers et al. |
| 6,175,752 | B1 | 1/2001 | Say et al. |
| 6,299,583 | B1 | 10/2001 | Eggers et al. |
| 6,336,045 | B1 | 1/2002 | Brooks |
| 6,473,641 | B1 * | 10/2002 | Kodama et al. ............... 600/547 |
| 6,491,647 | B1 | 12/2002 | Bridger et al. |
| 6,512,949 | B1 | 1/2003 | Combs et al. |
| 6,577,893 | B1 | 6/2003 | Besson et al. |
| 6,871,084 | B1 | 3/2005 | Kingsley et al. |
| 7,161,362 | B2 | 1/2007 | Shambroom et al. |
| 7,477,937 | B2 | 1/2009 | Iijima et al. |
| 7,931,592 | B2 | 4/2011 | Currie et al. |
| 8,085,144 | B2 | 12/2011 | Appelt et al. |
| 2002/0107452 | A1 | 8/2002 | Kwong |
| 2004/0128088 | A1 | 7/2004 | Laletin et al. |
| 2005/0113650 | A1 | 5/2005 | Pacione et al. |
| 2005/0245839 | A1 * | 11/2005 | Stivoric et al. ............... 600/549 |
| 2006/0085049 | A1 | 4/2006 | Cory et al. |
| 2006/0127964 | A1 * | 6/2006 | Ford et al. .................. 435/14 |
| 2007/0124176 | A1 | 5/2007 | Jung et al. |
| 2007/0178167 | A1 | 8/2007 | Andrijauskas |
| 2009/0054742 | A1 | 2/2009 | Kaminska et al. |
| 2009/0318779 | A1 | 12/2009 | Tran |
| 2009/0326407 | A1 * | 12/2009 | Tournefier et al. ............ 600/547 |
| 2010/0081941 | A1 | 4/2010 | Naghavi et al. |

FOREIGN PATENT DOCUMENTS

| | | |
|---|---|---|
| WO | WO-2006136598 A2 | 12/2006 |
| WO | WO-2011/070422 A1 | 6/2011 |

OTHER PUBLICATIONS

Allen, John: "Topical Review; Photoplethysmography and its application in clinical physiological measurement," IOP Publishing, vol. 28, No. 3. Mar. 1, 2007, pp. R1-R39.

Li, Jin et al; "Computation of Cardiac Output by Pulse Wave Contour," IEEE, 2007, pp. 1088-1090.

Awad, Aymen A. et al.; "The Relationship Between the Photoplethysmographic Waveform and Systemic Vascular Resistance," Journal of Clinical Monitoring and Computing, vol. 21, No. 6, Oct. 17, 2007, pp. 365-372.

Wang, L. et al.; "Noninvasive Cardiac Output Estimation Using a Novel Photoplethysmogram Index," 31st Annual International Conference of the IEEE EMBS, Minneapolis, MN, Sep. 2-6, 2009, pp. 1746-1749.

Cronin, Jane; Mathematics of Cell Electrophysiology, vol. 63, 1981, p. 23.

Chizmadzhev, Yuri A., et al.; "Electrical Properties of Skin at Moderate Voltages: Contribution of Appendageal Macropores," Biophysical Journal, vol. 74, Feb. 1998, pp. 843-856.

Atkins, Peter, et al.; "Atkins' Physical Chemistry," Eighth Edition, 2006, pp. 1-1053.

Brunswick, P., et al.; "Use of Ni electrodes chronoamperometry for improved diagnostics of diabetes and cardiac disease;" Proceedings of the 29th Annual International Conference of the IEEE EMBS, Lyon France, Aug. 23-26, 2007; pp. 4544-4547.

* cited by examiner

FIG. 4A

Pathology 1

| Name | Class | Purity | Age | MM | Mean FF | Mean FM | MP | Weight | Sex |
|------|-------|--------|-----|-----|---------|---------|-----|--------|-----|
| R002 | 1 | 90,90% | | [39; 87] | [11,5; 37] | | | [55; 76] | F |
| R003 | 1 | 90,50% | [52; 70] | | [11; 24] | [12,5; 28,5] | | [45; 87] | |
| R004 | 1 | 95,50% | [51; 70] | | [11,5; 48,5] | | [38,5; 88] | [45; 72] | |
| R005 | 0 | 96,50% | [18; 55] | [35,5; 82,5] | [16; 64,5] | | | [62; 109] | |
| R006 | 0 | 92,70% | | [36,5; 82,5] | | | | [55; 99] | M |
| R007 | 0 | 94,40% | [18; 57] | | | [21,25; 59,25] | [80,96; 5] | | |
| R008 | 0 | 94,50% | | | | [15,5; 59,25] | [57,5; 96,5] | [60; 109] | |

1 - ill
0 - not ill

MM     electrochemical conductance means MDMG et MGMD
Mean FF     electrochemical conductance means FDFG FGFD
Mean FM     FD and FG electrochemical conductances mean of anodes
MP     electrochemical conductance means PDPG et PGPD

FIG. 4B

Pathology 2

| Name | Class | Purity | Age | Mean FF | MM | MP | Weight |
|------|-------|--------|-----|---------|-----|-----|--------|
| R004 | 0 | 100% | [21; 71] | [16; 58,46] | | [64,8; 86,75] | [53; 86,7] |
| R005 | 0 | 100% | [21; 64] | [5,17; 56,32] | [41,41; 76,99] | | |
| R006 | 0 | 100% | [56; 68] | | [38,16; 45,12] | [51,49; 77,74] | |
| R001 | 1 | 100% | [53; 81] | [12,22; 63] | | | [73; 104] |
| R002 | 1 | 100% | | [7,2; 57,6] | [23,1; 74] | [23,25; 74,92] | [68; 104] |

FIG. 5A

| V | V (voltage) |
|---|---|
| $V_{PD}$ | V right foot |
| $V_{FD}$ | V right forehead |
| $V_{FG}$ | V left forehead |
| $V_{MG}$ | V left hand |
| $V_{MD}$ | V right hand |
| $V_{PG}$ | V left foot |

FIG. 5B

| V | Voltage |
|---|---|
| $V_C$ | Cathode voltage |
| VSa | Anode threshold voltage |
| VSc | Cathode threshold voltage |
| VSe | Electrode threshold voltage |

FIG. 5C

| VSa | Anode threshold voltage |
|---|---|
| VSc | Cathode threshold voltage |
| VSe | Electrode threshold voltage |
| FD-FG | Right forehead-Left forehead |
| FG-FD | Left forehead-Right forehead |
| MD-MG | Right hand-Left hand |
| MG-MD | Left hand-Right hand |
| PD-PG | Right foot-Left foot |
| PG-PD | Left foot-Right foot |

FIG. 6

| MM | Average electrochemical conductance RIGHT HAND-LEFT HAND and LEFT HAND-RIGHT HAND |
|---|---|
| Mean FF | Average electrochemical conductance RIGHT FOREHEAD-LEFT FOREHEAD and LEFT FOREHEAD-RIGHT FOREHEAD |
| Mean FM | Average anode conductances RIGHT FOREHEAD and LEFT FOREHEAD |
| MP | Average electrochemical conductance RIGHT FOOT-LEFT FOOT and LEFT FOOT-RIGHT FOOT |
| 1 | ill |
| 0 | not ill |

ELECTROPHYSIOLOGICAL ANALYSIS SYSTEM

CROSS-REFERENCE TO RELATED APPLICATIONS

This application is a continuation of U.S. patent application Ser. No. 12/527,415, filed on Aug. 14, 2009, issued on Feb. 18, 2014 as U.S. Pat. No. 8,655,443, which is a U.S. National Phase Entry of International Application No. PCT/EP2008/052211, filed on Feb. 22, 2008, which claims priority to French Application Serial No. 0753461, filed on Feb. 23, 2007, all of which are incorporated by reference herein.

BACKGROUND AND SUMMARY

This invention relates in general to medical diagnostic devices and methods in the field of human and animal health.

Considering the cost of blood tests and the invasive nature of exploratory blood sampling, physicians are increasingly reluctant to prescribe full assessments too frequently for their patients.

This results in an obvious under-detection of certain diseases the detection of which is made primarily by blood testing, such as diabetes, hypertension, hyperthyroidism, coronary diseases, . . . .

Furthermore, when these diseases are detected, it is often very difficult or costly to evaluate the effectiveness of the prescribed treatment, because, in actual practice, it is impossible to conduct daily bioanalyses.

In addition, various electrophysiological measurement systems are known, such as electrocardiography or electroencephalography apparatuses. These systems are passive in the sense that they measure electrical phenomena produced naturally by the human body, and have the advantage of being non-invasive, however the diagnostic possibilities of same are limited.

So-called active electrophysiological measurement systems are likewise known, which are based on impedance measurement. The operating principle of these apparatuses consists in running currents between various electrodes placed on the body, and in examining the way in which certain regions of the body attenuate this current. As a matter of fact, these rather high-frequency techniques have the disadvantage of depending heavily on the skin/electrode interface and, in particular, on the capacitive effect thereof. The reproducibility of measurements between patients, or even on one patient, is subject to reserve for these high-frequency measurements. As for very low-frequency measurements, they can be harmful to cells.

In addition, diagnostic systems are already known in which rectangular-wave voltages of a certain frequency are applied to electrodes placed on the fingers of a single hand, which frequency is necessarily high in order to be capable of detecting capacitive phenomena on the skin, and the current flowing in this portion of the body in response to this rectangular-wave voltage is studied. This system has evolved in order to incorporate a Fourier analysis in connection with the high frequency of the waves, which provides spectral distribution of the current observed. However, this known system has applications which are limited to very localized detections (in the area of the fingers of the hands and the feet), and enables diagnoses to be made only within the limits of conventional acupuncture techniques.

The applicant has already succeeded in broadening the diagnostic possibilities of electrophysiological-type systems by enabling same to detect a certain number of illnesses, diseases, pathological areas or other disorders normally detectable by testing blood or another bodily fluid.

The applicant has thus developed a simple-to-use, non-invasive diagnostic system having degrees of specificity and sensitivity which are equivalent to laboratory tests and which enables certain diseases, certain pathological predispositions or certain organ dysfunctions to be detected with improved reliability and with a broader range of possibilities.

This analysis system is described in the document FR-A-2 887 427.

This invention aims to propose an improved system, which, in particular, makes it possible to take account of the evolution of electrochemical phenomena occurring in the body based on the level of voltage to which the electrodes are subjected.

The invention likewise aims to propose a method of processing data with a view to developing a diagnosis, which is capable of taking account of measurements revealing such electrochemical phenomena.

To that end, according to a first aspect, an electrophysiological analysis system is proposed, which is intended, in particular for the detection of pathological conditions, characterised in that it includes:

a series of electrodes capable of being placed at various regions of the human body distant from one another, an adjustable DC voltage source which, in response to the control circuit, is capable of producing successive waves of a DC voltage which varies from one wave to the other, the duration of the waves being greater than or equal to approximately 0.2 second, a switching circuit capable of selectively connecting a pair of so-called active electrodes to the voltage source, and of connecting at least one other high-impedance electrode, and a measuring circuit capable of collecting data representative of the current in the active electrodes and of the potentials on at least some electrodes connected in high impedance, in response to the application of said waves, and in that, from one wave to the other, the range of voltages covered by the waves is capable of causing the appearance or disappearance of electrochemical phenomena in the vicinity of the active electrodes.

Certain preferred but non-limiting aspects of this system are as follows:

The system further includes a processing device capable of analyzing the reciprocal evolution of said current and said potentials in relation to the voltage of the waves, and of comparing such evolution to at least one reference evolution.

The switching circuit is capable of successively connecting various pairs of active electrodes to said voltage source.

When a pair of electrodes is connected to the voltage source, the switching circuit is capable of connecting all of the other high-impedance electrodes.

The measuring circuit includes a resistor capable of being connected between one of the electrodes of an active pair and a reference voltage.

The system likewise includes a calibration circuit which, for a given pair of active electrodes, is capable of adjusting the value of the measurement resistor so that it is of the same order of magnitude as the resistance present between the two active electrodes in the presence of a DC voltage.

The calibration circuit is capable of adjusting the value of the measurement resistor so that it is close the resistance of the human body.

The data representative of the current in the active electrodes derives from the potential difference measured at the terminals of the measurement resistor.

The measuring circuit is capable of measuring the potentials on all of the electrodes.

The voltage waves have a voltage value of between approximately 1 and 4 volts and a duration of between approximately 0.5 and 5 seconds.

The voltage of the successive waves varies in one direction and then in another.

The voltage of the successive waves varies by a first step, and then by a second step, which is smaller than the first.

The voltage of the successive waves varies in step between approximately 0.05 and 1 volt The successive waves are spaced apart by a duration of between approximately 0.5 and 5 seconds.

The switching circuit is capable of connecting a single pair of electrodes to the voltage source in two reversed polarities.

The system includes two electrodes for left and right frontal lobes, two electrodes for left and right hands and two electrodes for left and right feet.

The switching circuit is capable of connecting, to the voltage source, electrode pairs consisting of the left forehead electrode and the right forehead electrode, the right forehead electrode and the left forehead electrode, the left hand electrode and the right hand electrode, the right hand electrode and the left hand electrode, the left foot electrode and the right foot electrode and the right foot electrode and the left foot electrode.

After having connected a certain pair of electrodes to the voltage source with a certain polarity, the switching circuit is capable of connecting this same pair of electrodes to the voltage source with a reversed polarity, only after another distant pair of electrodes on the body has been connected to the voltage source.

According to a second aspect of the invention, a method is proposed for diagnosing a patient, with a view to detecting a disease, a pathological predisposition or another disorder, characterised in that it includes the following steps:

receiving a set of data comprising measurements revealing electrochemical phenomena in the vicinity of the electrodes applied to the skin of the patient at predetermined locations on the body, accessing at least one set of stored reference data comprising measurements revealing electrochemical phenomena, which were obtained under the same conditions, on patients identified as suffering or not suffering from this disease, and reconciling said set of data received with the sets of reference data, and, based on proximity criteria between the set of data received and the sets of reference data, identifying the patient as ill or not ill.

Preferred but non-limiting aspects of this method are as follows:

The data sets further include data of a physiological and/or behavioural and/or environmental nature.

The data sets comprise measurements taken on a patient after a predetermined exertion by the patient.

The measured data is obtained from current values in the active electrodes and from potential values on high-impedance electrodes, in response to the application of voltage waves between active electrodes, the level of which varies from one wave to the other, in order to cause the appearance or disappearance of electrochemical phenomena in the vicinity of the active electrodes.

Said measurements are provided by a system as defined above.

The method is implemented in computer equipment which is remote from the system and connected thereto via a data communication channel.

BRIEF DESCRIPTION OF THE DRAWINGS

Other aspects, objectives and advantages of this invention will become more apparent upon reading the following detailed description of preferred embodiments thereof, which is given for non-limiting purposes and made with reference to the appended drawings, in which:

FIGS. 5A-5C and 6 are tables showing abbreviations used.

DETAILED DESCRIPTION

An electrophysiological measurement diagnostic system according to the invention will now be described. This system is founded on an active operating principle, in direct-current mode, as distinguished, in particular, from the impedance measurement systems of the prior art, the disadvantages of which were recalled above.

Following a certain number of tests, the applicants observed that the application of a low DC voltage at the terminals of a pair electrodes distant from one another (anode and cathode), produced different electrochemical behaviours at the anode and cathode.

In particular, it was observed that chloride ions Cl− react to the anode, whereas a reaction to hydrogen ions is witnessed at the cathode. One object of the invention is to be able to differentiate between the behaviour of the anode, on the one hand, and the cathode, on the other hand.

Based on this principle, the applicants discovered that it was possible to use the electrodes in two ways, one in the presence of a current and under a potential difference, which can vary so as to observe the evolution of the electrochemical phenomena at the anode and at the cathode, and the other in the presence of a negligible (high-impedance) current in at least one other electrode, so as to observe the evolution of the intermediate potentials of the body. This makes it possible to evaluate the anode and cathode voltage drops separately, and to therefore evaluate the Cl− and H+ levels separately.

In this regard, tests on patients suffering from certain diseases made it possible to demonstrate that different behaviours, in terms of static resistance and electrochemical voltage, could be indicative of such diseases. For example, certain variations in pH at the cathode, which were detected by variations in resistance, can reveal disorders of the acidosis and alkalosis type, whereas certain variations in the concentration of chloride ions at the anode can enable diagnosis of diseases such as cystic fibrosis.

These measurements of chloride concentrations and reactivity of the acid-base equilibrium are capable of tracing homeostatic, hormonal, vascular, metabolic, etc. dysfunctions. These dysfunctions may themselves correspond to physiological conditions indicative of diseases or various pathological predispositions, in particular:

vascular (hypertension and extensive atheroma);
hormonal (hypo- and hyperthyroidism, etc.);
metabolic (diabetes, etc.);
chronic (renal failure, etc.);
but also indicative of the effect of certain medical or other types of treatments.

The system of the invention, as will now be described in detail, aims to exploit the aforesaid phenomena or similar phenomena.

Figure 1:
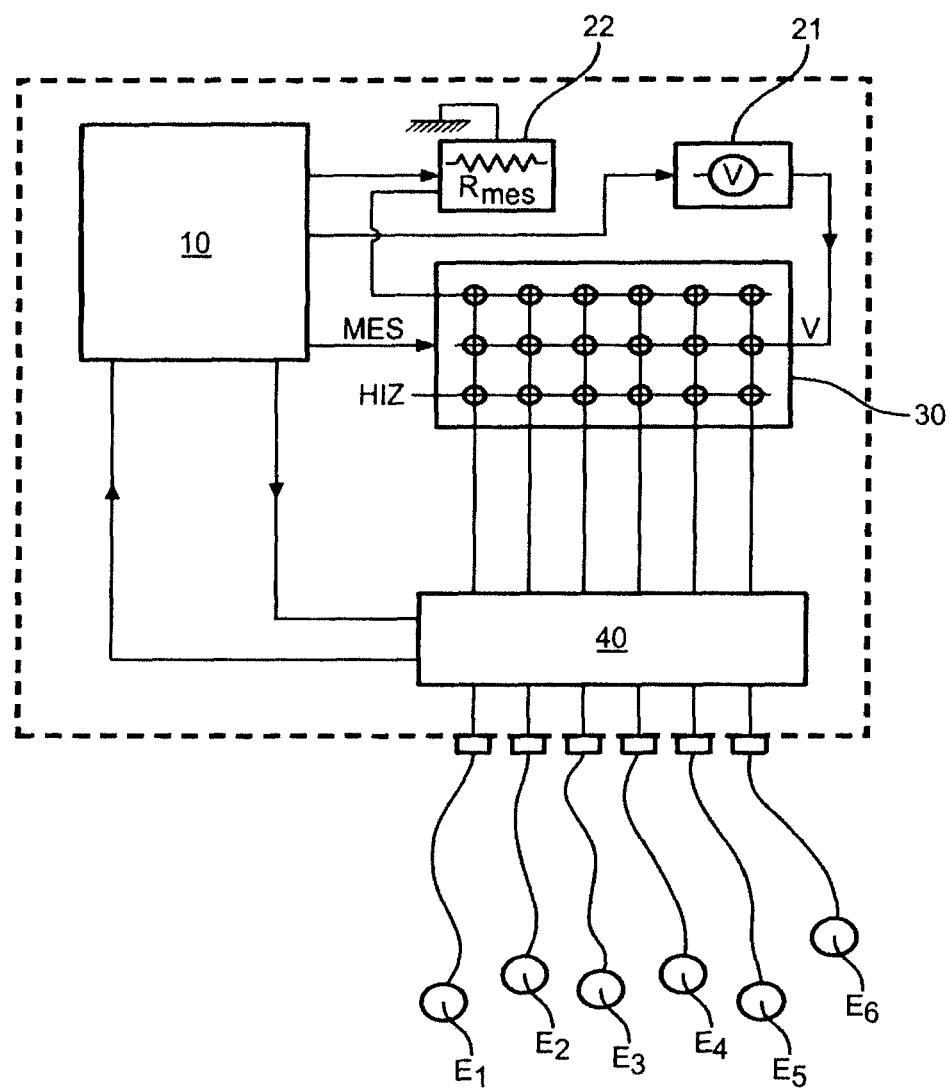
FIG. 1 is a block diagram showing the various functional elements of an acquisition system according to this invention.

With reference to FIG. 1, a schematic representation has been shown of a system for diagnosing via electrophysiological measurements, which is capable of exploiting the aforesaid principles, and which, in an appropriate housing (not shown), includes a central processing unit 10 comprising, for example, a microprocessor associated with suitable storage devices as well as with inputs/outputs, e.g., for a control keyboard and a display device.

This central unit controls an electrical voltage generator 21 which, in response to suitable control signals, is capable of producing waves of a constant but adjustable voltage for each of the waves. The duration of the waves, which, at a minimum, is 0.2 second, and typically between 0.5 and 5 seconds, is likewise optionally adjustable.

The central unit 10 likewise applies control signals to a control circuit forming a measurement resistor 22 which, as will be seen, is capable of being connected between an electrode and a reference voltage such as the ground (0 volt), and of having a voltage to be measured at the terminals thereof, which is directly proportional to the current passing through same. Adjusting the ohmic value of this resistor enables the voltage measurement to be optimised in relation to the observed current level, as will be seen hereinbelow.

This circuit forming a variable measurement resistor is typically a digitally-controlled potentiometer.

The system likewise includes an electronic switching circuit which, on each of N terminals, is capable of either applying thereto the voltage waves produced by the circuit 21, of connecting thereto the measurement resistor 22, or else of placing this terminal in high impedance, wherein, in a conventional manner known per se, it can be seen as grounded by a very high ohmic value resistor.

The switching circuit 30 reacts to control signals supplied by the central unit in order to modify the connections of the N terminals according to various sequences, as will be seen in detail below.

The system also includes a measuring circuit 40 which is responsive to instructions from the central unit in order to sequentially or simultaneously measure the voltages present at a given moment on each of the N terminals of the switching circuit. This circuit advantageously makes use of conventional techniques for analogue/digital conversion on several inputs and for multiplexing.

The N terminals of the switching circuit are also connected to N connectors enabling the electrical connection of N electrodes per unit area En.

In this exemplary embodiment, the number N is equal to 6, and the 6 electrodes connected are intended to be placed in the region of the both frontal lobes, both hands or wrists, and both feet or ankles of a patient.

In this way, a certain number of measurement possibilities are obtained, as will be seen in detail hereinbelow.

The central unit is likewise capable of processing all of the information and data put into play within the system, this data primarily comprising, in relation to time, the voltage level produced at the generator 21 level, the value of the measurement resistor 22, and the voltage levels recorded, simultaneously or quasisimultaneously, at the six terminals of the switch, and therefore at the six electrodes E1 to E6. As will be described in detail, this processing has the purpose of detecting and in particular, of visually signalling the existence of a physiological condition related to a pathological predisposition, to the taking or not taking of a treatment, or to a disease or other disorder.

Alternatively, this detection processing can be carried out with remote equipment, after having loaded onto same (via a physical medium or via a wired or wireless network communication) all of the data collected by the central unit 10 and stored therewithin.

The electronic switching circuit 30 makes it possible to sequentially select two electrodes as an anode Ea and cathode Ec, the first being connected to the voltage generator 21 and the second being connected to the measurement resistor Rmes of the unit 22. During this time, the other electrodes (in this case, the four others, referenced as Eb1 to Eb4) are connected in high impedance.

Figure 2:
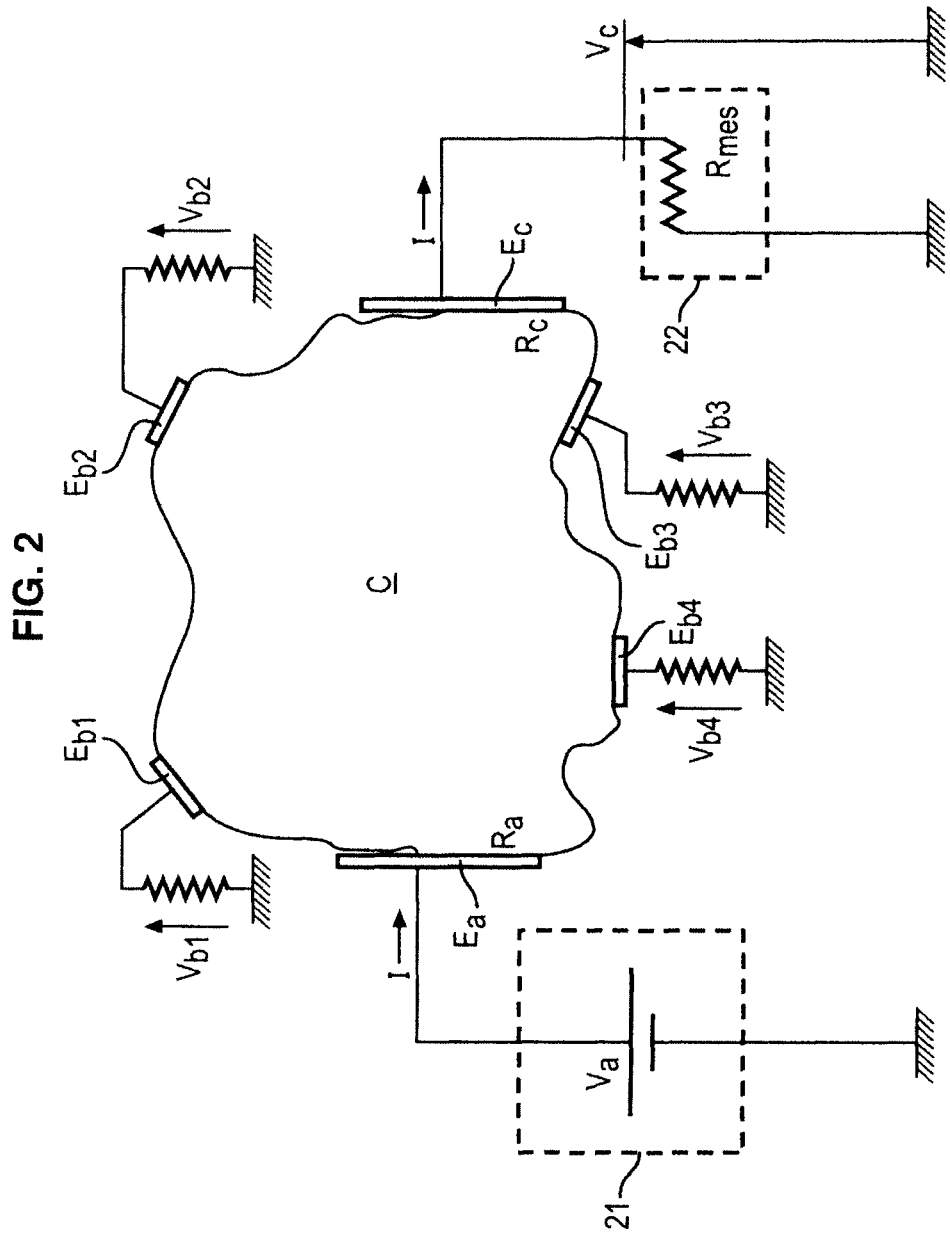
FIG. 2 shows the equivalent circuit diagram of the system of FIG. 1, when the electrodes are connected at various locations on the human body.

The equivalent electrical circuit is shown in FIG. 2. The measuring circuit 40 is capable of measuring, with a suitable sampling frequency, e.g., of the order of 100 to 10,000 Hz, the voltages present on each of the 6 electrodes, the anode voltage Va being equal to the voltage supplied by the voltage generator 21, while the cathode voltage Vc, via knowledge of the ohmic value of the resistor Rmes, determines the value of the current I flowing in the electrodes Ea and Ec. In this case, the extremely weak current which may be flowing in the electrodes Eb1 to Eb4 is ignored, the high-impedance connection of which is shown by the resistors Rb1 to Rb4 having a value typically greater than 10 MΩ.

The potentials on the electrodes Eb1 to Eb4 are designated by Vb1 to Vb4, respectively.

It shall be observed that, in practice, besides the evolution over time of voltages Va and Vc, the central unit 10 can examine either the evolution of the four voltages Vb1 to Vb4 individually, or the evolution of an average of these values, referenced here as Vb.

The device as described above is controlled by the central unit 10 so as to carry out a certain number of operations.

The first operation is an automatic calibration, carried out once the electrodes have been installed on the patient.

In this way, for each pair of electrodes which will be used as a couple (anode, cathode), and, for example, the pair of forehead electrodes, the pair of hand electrodes and the pair of feet electrodes, the device 10 causes a DC voltage, e.g., of the order of 2 volts, to be a applied to the anode, and adjusts the value of the resistor Rmes so as to obtain a stabilized cathode voltage of approximately half (or a specific fraction of preferably between 0.1 to 0.9) of the anode voltage. This results in adjusting the Rmes so that it is close (at least of the same order of magnitude) to the resistance present between these two electrodes, which cumulates the electrode/skin contact resistances and the resistance of the body between the two mutually distant regions of the body. The optimal Rmes values for each of the pairs (anode, cathode) which will next be used for the actual measurements, as will be described below, are stored one-by-one, in the form of the control signals thereof, and will be recalled by central unit based on the pair (anode, cathode) involved.

For each pair (anode, cathode), this automatic calibration step makes it possible to use the Rmes value which offers the best dynamics and the best resolution for measuring the evolution of the current which passes into the pair of electrodes in question during the actual measurements, it being specified that the resistance present between the electrodes can vary greatly based, in particular, on the surface area of the electrodes, the quality of the electrode-skin contact and the ageing of the electrode material.

Of course, if necessary, these automatic calibration operations can be duplicated for the case where an anode/cathode electrode pair becomes a cathode/anode electrode pair, which is obtained by swapping the connections for the two electrodes at the switching circuit 30.

The actual measurements are carried out by first selecting pair of active electrodes (anode, cathode), and by adjusting Rmes to the appropriate value thereof, as described above.

A series of DC voltage waves of a sufficient duration (of the order of 0.5 to 5 seconds) are then applied in order to achieve a certain stabilisation of the current I, by starting with a high level of voltage (typically of the order of 4 volts, approximately half of which is at the terminals of the electrodes, for the reasons explained above), down to a low level of voltage (typically of the order of 1 to 2 volts), with a step of the order of 0.05 to 0.5 volt between two successive waves. An increasing evolution is, of course, likewise possible.

During each voltage wave controlled by the central unit 10, the latter simultaneously controls the measuring circuit 40 so as to record the potential present on each of the six electrodes, with the specific sampling frequency (preferably between 100 and 10,000 Hz, as indicated above).

Amongst these potentials, the potential Va is representative of the voltage produced by the generator 21, while the potential Vc is directly proportional to the current I flowing in the anode Ea and cathode Ec, and enables same to be calculated, if necessary.

The other potentials are those observed at the other locations of the body onto which the other electrodes are applied, but through which a substantially zero current (high impedance) passes.

The above measurements are carried out for several pairs of active electrodes.

Typically, with a six-electrode system as described above, the measurements are carried out with the following pairs of electrodes (abbreviated designation between parentheses):

| Anode | Cathode |
|---|---|
| left forehead (FG) | right forehead (FD) |
| right forehead (FD) | left forehead (FG) |
| left hand (MG) | right hand (MD) |
| right hand (MD) | left hand (MG) |
| left foot (PG) | right foot (PD) |
| right foot (PD) | left foot (PG) |

For each pair of electrodes, the evolution of the current during each of the waves is primarily related to the dynamics for establishing the electrochemical phenomena with respect to the anode and the cathode, under a potential difference which is different each time.

The potential levels and the time-dependent evolution thereof over the course of the wave, not only at the cathode (Vc) but likewise on the passive electrodes Eb1 to Eb4 (Vb1 to Vb4), based on the voltage level Va of the wave in question, yield a certain amount of raw data that it is possible to process in a variety of ways.

According to one advantageous alternative, voltage waves can be provided the voltage level of which varies in one direction, and then in the other. More specifically, it is possible to provide for the voltage level to begin by increasing by a relatively rudimentary step, e.g., 0.2 to one volt, and to then continue by decreasing, by a smaller step, e.g., from 0.1 to 0.5 volt, once the appearance of an electrochemical phenomenon has been detected, as will be described hereinbelow.

To date, one particularly useful processing operation for detecting pathological predispositions, or diseases, which are related in particular to the concentration of chloride anions or to the pH value (concentration of hydrogen cations), consists in examining the evolution of curves reflecting the evolution of the voltages Vc and Vbi (or the average thereof) at the end of the wave, based on the value of the wave voltage Va, and this is carried out for each of the six pairs of electrodes.

More precisely, it was observed that such a curve was initially almost linear, and starting with a certain potential difference between the electrodes, the linearity disappeared, the curve curving with an increasing slope due to the occurrence of electrochemical phenomena.

It was likewise observed that the anode voltage level Va, starting at which the curve curves, as well the cathode voltage level Vc and the inactive electrode voltage levels Vb1 to Vb4 (or the average thereof Vb), were themselves indicative of certain disorders.

Figure 3A:
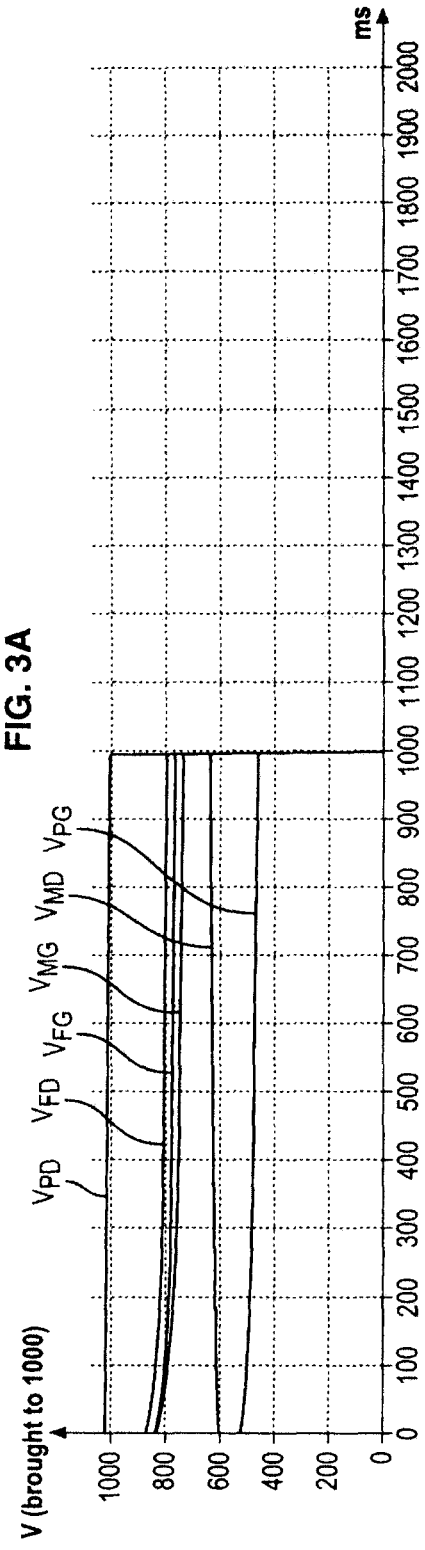
FIGS. 3A, 3B and 3C are diagrammed screen images produced by a data processing system associated with the acquisition system of FIG. 1, FIGS. 4A and 4B are tables of sets of reference data implemented in a data processing method, with a view to a diagnosis according to the invention.
Figure 3C:
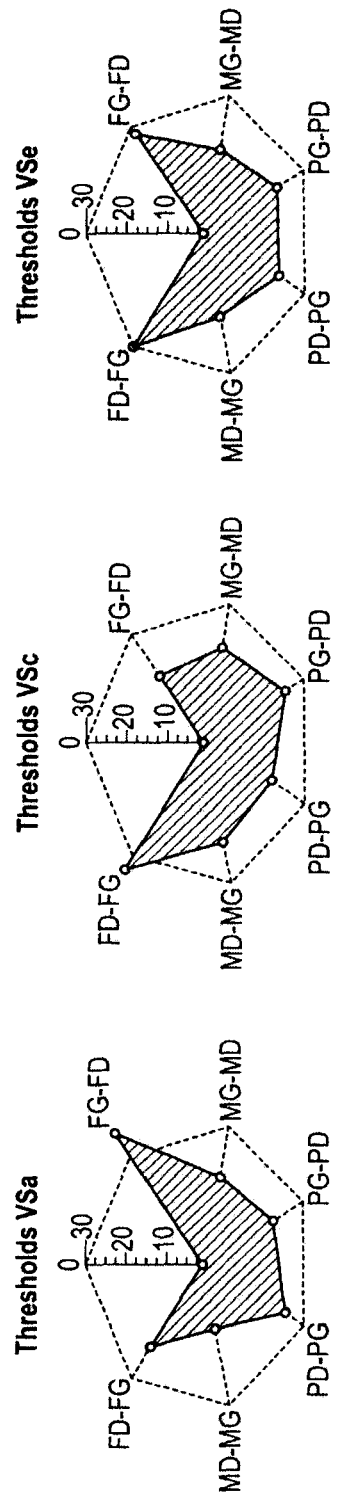
Figure 3B:
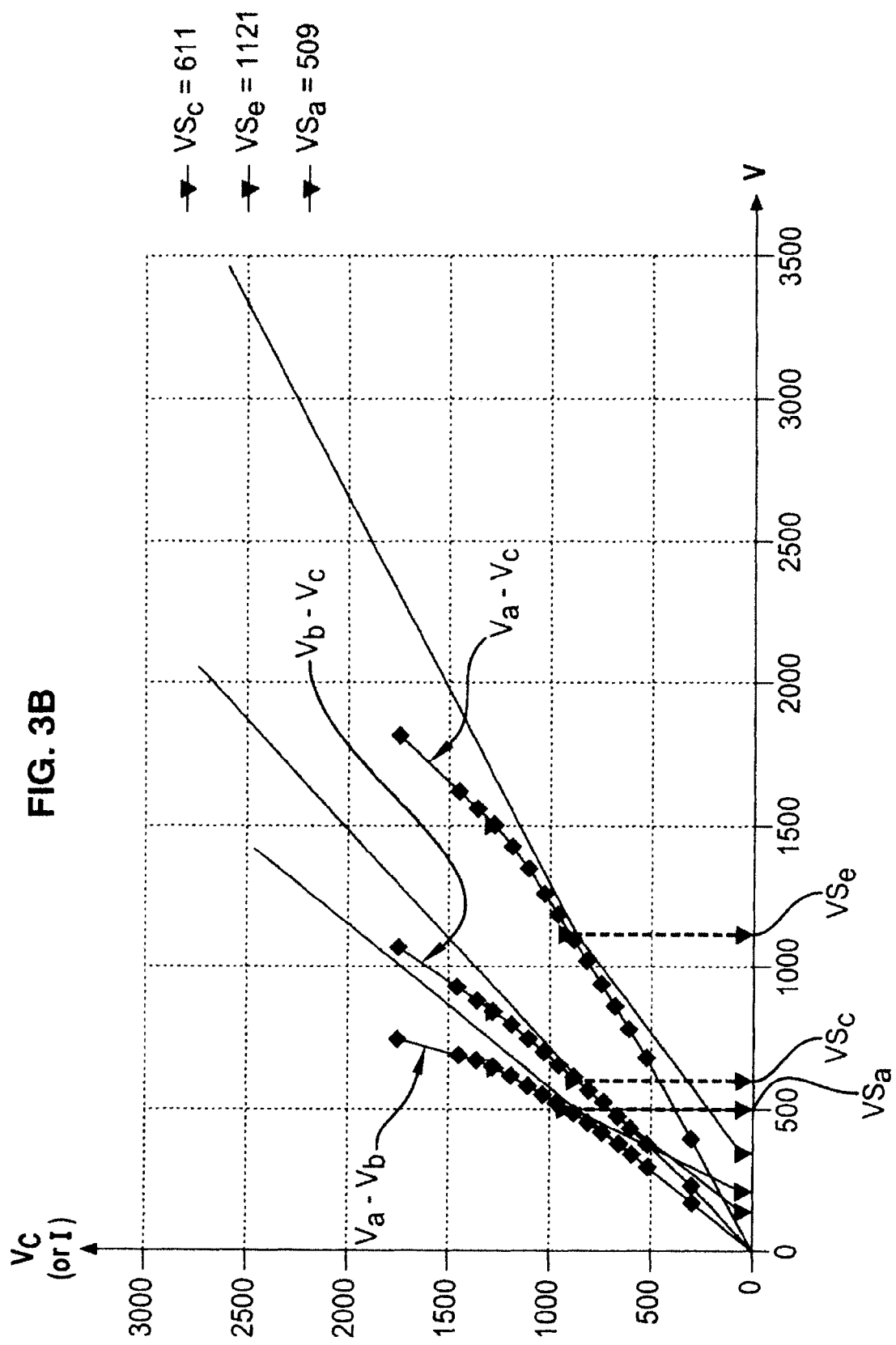

Thus, FIGS. 3A and 3B of the drawings show screen images delivered by a data processing system (either based on the central unit 10, or remote), on the basis of collected data.

FIG. 3A shows the evolution of the voltage levels recorded for each of the six electrodes, voltages which are designated by VFG, VFD, FMG, VMD, VPG, VPD, respectively, during application of a wave (in this case, having a duration of one second) in the example wherein the anode and the cathode Ea and Ec are the electrodes PD and PG, respectively. It is observed on these curves that the voltage VPD, which is the anode voltage produced by the generator 21, is quite constant over the entire duration of the wave, whereas the other measured voltages initially vary rather sharply (by increasing or decreasing), so as to begin to stabilise and to ultimately be stable at the end of the wave. It is the end of the wave voltage values, for a plurality of waves of different voltage levels, which are used to establish the curves shown in FIG. 3B.

These curves show the mutual evolution of the cathode voltage (i.e., of current I), appearing on the y-axis, and of the various potential differences Va–Vb, Vb–Vc and Va–Vc, the voltage appearing on the x-axis. These curves are constructed by the data processing system on the basis of the voltage values obtained at the end of each wave of the series of waves applied, as described above.

For each of these curves, it is observed that a voltage threshold value exists (VSa, VSc and VSe, respectively) for which this curve departs from the linear appearance thereof in order to curve, which is indicative of the appearance (or the disappearance, in the direction of the decreasing voltages) of an electrochemical phenomenon at the anode or cathode.

From these values, which each correspond to a given current value I and therefore to a given voltage value Vc, it is possible to obtain the value triplet VSa, VSc and VSe corresponding to these thresholds.

These treatments being carried out for each of the six pairs of electrodes chosen, for a given patient three sextuplets of values VSa, VSc, and VSe corresponding to these thresholds are obtained.

With reference now to FIG. 3C, it is possible to construct graphs from each of these three sextuplets, such as radar curves, which make it easy to visually compare the characteristics obtained for a given patient with model or reference curves corresponding to healthy patients or to given diseases or pathological dispositions. They likewise facilitate comparison with characteristics obtained previously with the same patient, in particular for monitoring the effect of a treatment.

Of course, a person skilled in the art will be able to conceive of numerous other processing operations on the data collected wave-by-wave, as described above, or even between waves, without departing from the scope of this invention, the uniqueness of which is found in the manner in which the data is collected.

Furthermore, and as will be described in detail hereinbelow, the various types of measurements can be combined in very different ways within the framework of a data processing method, with a view to diagnosing such or such disease, pathological evolution or pathological predisposition.

A normalisation functionality optionally provided in the system of the invention will now be described, which makes it possible to do without certain voltage measurement offsets, due, in particular, to the use of different electrode materials or to materials the ageing of which has an impact on behaviour upon contact with the skin. As a matter of fact, it has been observed that, depending on the nature of the electrode materials and the degree of wear or ageing thereof, the electrode/skin interfaces consisted of electrochemical cells generating variable voltages (plus or minus) of a few tens to a few hundreds of millivolts, which were capable of distorting the measurements. Once the electrodes have been placed on the patient, this functionality consists in connecting one of the electrodes to the voltage source, delivering, for example, a continuous value of 2 volts, in connecting the five other high-impedance electrodes, and in measuring the static potentials on these five other electrodes by means of the measuring circuit. These operations are repeated by applying the DC voltage successively to each of the five other electrodes.

In this way, by means of a fast operation, since it requires a few seconds per electrode configuration, a mapping operation is carried out, which makes it possible to calculate offset voltages which will be used to correct the measurements taken when the voltage waves are applied over the course of the acquisition process described above. More precisely, each time that a given electrode is selected as an anode, the offset voltages recorded when this same electrode was connected to the voltage source are used to correct the voltages recorded at the other electrodes by the measuring circuit.

In order to minimise the necessity of making the aforesaid corrections, all of the electrodes are preferably made of the same material. A material having a high nickel content is preferably chosen, for which it was possible to determine, via in vitro experiments, that it was the most suitable for carrying out electrochemical measurements involving chlorides. This is likely explained by a phenomenon involving activation of the surface of the nickel substrate by chloride ions. Alternatively, electrodes made of silver or a silver-rich alloy can be used, giving rise to electrochemical couples (Ag/AgCl) which may yield interesting measurements.

The surface of the electrodes is chosen to be as large as practicable, knowing that the electrodes are relatively rigid and must be capable of being in contact with the skin over their entire extent. A surface area of 2 to 100 cm2 will generally be chosen, based on the location of the body where the electrode is intended to be placed.

Of course, numerous alternatives to the system are possible.

In particular, it is possible to vary the number of electrodes, and, for example, to make use of eight electrodes (four for the ends of the limbs, two for the forehead and two for the chest).

Furthermore, the architecture of the system of the invention can be a wireless architecture of the type shown in FIG. 3 of the document FR-A-2 887 427, to which reference may be made for further details.

In the same way, a local or remote, real- or quasi-real time processing system can be combined with the present invention, according to the principles described, in particular, in the aforesaid document.

An exemplary data processing method for diagnostic purposes will now be described, which exploits the measurements of electrochemical phenomena, which are carried out, in particular, with a device as described above, and which is capable of being implemented locally or remotely.

Generally speaking, the method first consists in acquiring sets of multi-dimensional data measured across a patient population for which the disease or diseases are known, and, where relevant, with respect to patients already identified as healthy, in particular by means of a system as described above. These multi-dimensional measurements are completed with physiological, behavioural and/or environmental values of the patients, such as age, sex, weight, tobacco consumption, profession, living environment, etc.

It is likewise possible to take into consideration the evolution of these values over time, with appropriate spacing (from a few hours to several years).

The method can likewise take into consideration sets of multi-dimensional data before and after a predetermined exertion (stress test).

In this way, a set of reference data is created for a certain number of diseases, using known data mining techniques.

This data typically includes ranges of reference values for the various diseases, according to the various dimensions.

These sets of reference data can be advantageously enriched or refined from new acquisitions concerning afflicted patients, via iteration of the data mining process.

Furthermore, over the course of time, the sets of reference data can be refined using known learning techniques, e.g., based on state-of-the-art tools such as decision trees, neural nets or support vector machines.

Each set of multi-dimensional data which was obtained with the above-described system, with respect to patients being diagnosed, or else for whom a previous diagnosis requires confirmation or follow-up, and which was completed by available additional data (also input or stored), such as the sex and age of the patient, the habits and living environment thereof (and more generally any other physiological, behavioural environmental data, etc.) can then be reconciled with the set of reference data stored in association with the data processing unit responsible for implementing the method, by any suitable comparison technique (rescaled or non-rescaled sum of scores overlapping with or close to the reference data, etc.).

Prior to this reconciliation, and once again in a conventional manner known per se, the input data is normalised, if necessary.

A set of reference data obtained for chronic renal insufficiency is shown in the table of FIG. 4A.

In this example and in the following one, this set of data includes a set of N bytes of ranges of significant values obtained with a series of afflicted patients (Class=1) and with a series of unafflicted patients (Class=0), these bytes being designated by their names R002 to R008 and forming a cloud of multidimensional volumes in the space having N corresponding dimensions.

In this example, the various dimensions are as follows, with reference to FIGS. 5A-5C and 6:

the age of the patient (AGE),

MM: the average of electrochemical conductances MD-MG and MG-MD,

FF: the average of electrochemical conductances FD-FG and FG-FD,

FM: the average of anode conductances FD and FG,
MP: the average of electrochemical conductances PD-PG and PG-PD,
the weight of the patient (WEIGHT),
the sex of the patient (SEX).

It shall be noted here that the data purity index ("Purity" in the table of FIG. 4A) indicates a probability that the rule used corresponds to the indicated class.

Another exemplary set of reference data relating to an autonomic neuropathy-type disease is shown in FIG. 4B.

In one particular embodiment, the processing of data for diagnostic purposes is carried out with a remote server connected to the acquisition system, as described above, via a wireless communication channel (local or wide area network such as the Internet or GSM, with appropriate data securisation).

The diagnostic information can next be reproduced on any medium, whether paper or a display screen.

What is claimed is:

1. An electrophysiological analysis system for use on a patient, the system comprising:
    (a) a rigid right hand-electrode;
    (b) a rigid left hand-electrode;
    (c) a rigid right foot-electrode;
    (d) a rigid left foot-electrode;
    (e) a computer coupled to the electrodes, the computer receiving patient age or weight data;
    (f) a direct current voltage source controlled by the computer, the computer causing polarity to switch between the electrodes;
    (g) the computer using analogue-to-digital conversion to assist with measurements from the electrodes; and
    (h) a resistor electrically connected to at least one of the electrodes;
    (i) the computer operably determining if a patient disorder is present using variation information regarding pH at at least one of the electrodes which is a cathode or using variation information regarding a concentration of chlorides at at least one of the electrodes which is an anode.

2. The system of claim 1, wherein the hand electrodes are each sized to be in contact with a patient's hand over the entire extent thereof.

3. The system of claim 1, wherein the foot electrodes are each sized to be in contact with a patient's foot over the entire extent thereof.

4. The system of claim 1, wherein all of the electrodes are of the same material and the electrodes operably carry out electrochemical measurements involving the chlorides.

5. The system of claim 1, wherein the computer causes polarity reversal of the right and left electrodes.

6. The system of claim 1, further comprising diagnostic measurement data, related to electrochemical phenomena of the patient detected via the variations in the pH at the electrodes, is displayed on a display screen coupled to the computer.

7. The system of claim 1, wherein the computer assists in diagnosing cystic fibrosis via the concentration of the chlorides at the anode.

8. The system of claim 1, wherein the computer assists in diagnosing diabetes by displaying data in a radar curve on a display screen.

9. The system of claim 1, wherein the computer compares data detected by the electrodes in real-time with stored data previously obtained from the same patient for monitoring the effect of a diabetes treatment.

10. The system of claim 1, wherein the computer compares data detected by the electrodes in real-time with stored data previously obtained from the same patient for monitoring the effect of a cystic fibrosis treatment.

11. An electrophysiological analysis system for use on a patient, the system comprising:
    (a) a rigid right hand-electrode;
    (b) a rigid left hand-electrode;
    (c) a rigid right foot-electrode;
    (d) a rigid left foot-electrode;
    (e) a computer coupled to the electrodes which operably carry out electrochemical measurements involving chlorides of the patient;
    (f) a display screen coupled to the computer; and
    (g) a direct current voltage source coupled to the computer, and the computer causing polarity to switch between the electrodes, a direct current reference voltage being sent to at least one of the electrodes;
    (h) the computer comparing data detected by the electrodes in real-time with stored data previously obtained from the same patient for monitoring the effect of a cystic fibrosis treatment.

12. The system of claim 11, wherein the hand electrodes are each sized to be in contact with a hand of the patient over the entire extent thereof.

13. The system of claim 12, wherein the foot electrodes are each sized to be in contact with a foot of the patient over the entire extent thereof.

14. The system of claim 11, wherein all of the electrodes are of the same material, and the electrodes are suitable for carrying out electrochemical measurements involving pH of the patient.

15. The system of claim 11, wherein the computer causes polarity reversal of the right and left electrodes, further comprising diagnostic measurement data, related to electrochemical phenomena of the patient detected via variations in pH at the electrodes, is displayed on the display screen.

16. The system of claim 11, wherein the computer compares the data detected by the electrodes in real-time with stored reference data previously obtained from reference healthy and reference cystic fibrosis patients, and visually displays a graph of the compared data.

17. An electrophysiological analysis system for use on a patient, the system comprising:
    (a) a right hand-electrode having a metallic surface sized to contact with skin over the entire extent of a hand of the patient;
    (b) a left hand-electrode having a metallic surface sized to contact with skin over the entire extent of a hand of the patient;
    (c) a right foot-electrode having a metallic surface sized to contact with skin over the entire extent of a foot of the patient;
    (d) a rigid left foot-electrode having a metallic surface sized to contact with skin over the entire extent of a foot of the patient;
    (e) a computer coupled to the electrodes; and
    (f) a direct current voltage source coupled to the computer, and the computer causing polarity to switch between the electrodes;
    (g) the electrodes operably sending signals to the computer responsive to at least one of: electrochemical measurements involving chlorides or pH, of the patient adjacent the electrodes;
    (h) the computer comparing data detected by the electrodes in real-time from the patient with stored data previously obtained to assist in detection of at least one patient illness comprising: (i) cystic fibrosis, or (ii) diabetes; and (i) the computer processing a resistance value based on at least some of the signals.

18. The system of claim 17, wherein the computer causes the polarity reversal of the right and left electrodes, further comprising a display screen displaying diagnostic measurement data related to electrochemical phenomena of the patient detected via variations in pH at the electrodes, and the computer comparing the real-time data with the stored reference data previously obtained from reference healthy and reference cystic fibrosis patients, and visually displaying a graph of the compared data.

19. The system of claim 17, wherein all of the electrodes are of the same material, and the electrodes are suitable for carrying out electrochemical measurements involving pH of the patient.

* * * * *